United States Patent [19]

Uphues et al.

[11] Patent Number: 5,569,767
[45] Date of Patent: Oct. 29, 1996

[54] PROCESS FOR THE PRODUCTION OF LOW-VISCOSITY STORABLE AMPHOTERIC SURFACTANTS FROM IMIDAZOLINES

[75] Inventors: Guenter Uphues, Monheim; Uwe Ploog; Renate Schick, both of Haan; Hans-Juergen Schwark, Monheim; Sandra Witt, Langenfeld, all of Germany

[73] Assignee: Henkel Kommanditgesellschaft auf Aktien, Duesseldorf, Germany

[21] Appl. No.: 436,324

[22] Filed: Jul. 25, 1995

[30] Foreign Application Priority Data

Nov. 30, 1992 [DE] Germany .......................... 42 40 154.2

[51] Int. Cl.$^6$ .................... C07D 233/04; C07D 233/14; C11D 1/88
[52] U.S. Cl. .................... 548/352.1; 252/356; 252/357; 510/237; 510/480; 510/490; 510/535
[58] Field of Search .......................................... 548/352.1

[56] References Cited

U.S. PATENT DOCUMENTS

| | | | |
|---|---|---|---|
| 2,773,168 | 12/1956 | Mannheimer | 260/309.6 |
| 4,269,730 | 5/1981 | Wechsler et al. | 252/356 |
| 4,833,253 | 5/1989 | Ploog et al. | 548/352.1 |
| 5,342,961 | 8/1994 | Uphues et al. | 548/352.1 |

FOREIGN PATENT DOCUMENTS

| | | | |
|---|---|---|---|
| 0040346 | 11/1981 | European Pat. Off. | 548/352.1 |
| 0001006 | 12/1981 | European Pat. Off. | 548/352.1 |
| 2063424 | 7/1972 | Germany | 548/352.1 |
| 3639752 | 5/1987 | Germany | 548/352.1 |
| 3641871 | 6/1988 | Germany | 548/352 |
| 4038983 | 6/1992 | Germany | 548/352.1 |
| 0850514 | 10/1960 | United Kingdom | 548/352.1 |
| 0930296 | 7/1963 | United Kingdom | 548/352.1 |

OTHER PUBLICATIONS

Seifen–Fette–Ole–Wachse, 108, 373 (1982) (Ploog).
J. Am. Oil. Chem. Soc., 60, 1807 (1983) (Takano et al.).

*Primary Examiner*—Floyd D. Higel
*Attorney, Agent, or Firm*—Wayne C. Jaeschke; John E. Drach; Henry E. Millson, Jr.

[57] ABSTRACT

In order to prepare fluid, storage-stable ampholytic surface-active agents, (a) 1-hydroxyethyl-2-alkyl-2-imidazolines having formula (1), in which $R^1$ stands for an alkyl residue with 5 to 21 carbon atoms, are quaternated or carboxymethylated with halogenated carboxylic acid salts at a pH range from 7.5 to 9, and at the same time hydrolyzed with aqueous bases, then (b) the pH value of the reaction final products is set between 5 and 7.

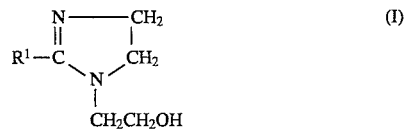

14 Claims, No Drawings

PROCESS FOR THE PRODUCTION OF LOW-VISCOSITY STORABLE AMPHOTERIC SURFACTANTS FROM IMIDAZOLINES

BACKGROUND OF INVENTION

1. Field of the Invention

This invention relates to a process for the production of low-viscosity, storable amphoteric surfactants in which imidazolines are quaternized or carboxymethylated, hydrolyzed and stored in narrow pH ranges.

2. Statement of Related Art

Amphoteric surfactants, more particularly of the imidazolinium betaine type, have favorable foaming and cleaning properties and are acquiring increasing significance as co-surfactants in manual dishwashing detergents and cosmetic cleansing and personal care products [Seifen-Fette-Öle-Wachse, 108, 373 (1982)]. Surfactants such as these are normally obtained by alkylation of imidazolines with sodium chloroacetate and subsequent or simultaneous hydrolysis of the imidazoline ring. A particular problem of the production process is to obtain amphoteric imidazolinium surfactants which have low viscosities, even in the event of prolonged storage, and which are therefore easy to pump and dose.

There has been no shortage of attempts in the past to produce amphoteric surfactants of the imidazoline betaine type. Two different routes have been adopted for this purpose, namely:

1. Single-stage process: the reaction with sodium chloroacetate takes place after the hydrolysis of the imidazoline ring [cf. GB-A 850,514, GB 930,296, U.S. Pat. No. 2,773,168, EP-B 0 040 346 (Henkel), DE 36 39 752 (Kao)]. According to the teachings of these documents, however, highly viscous products with a target solids content of around 50% by weight are always obtained.

2. Two-stage process: in the first step, the imidazoline is reacted to the betaine which is then hydrolyzed, i.e. ring-opened, in the presence of bases before reacting off with more sodium chloroacetate [cf. DE 20 63 424 (Rewo), U.S. Pat. No. 4,269,730 (Stepan), EP-B-0 001 006 (Albright & Wilson), DE 40 38 983 (Henkel)]. Although products produced in this way are of low viscosity, even in highly concentrated form, immediately after their production, they undergo a rapid increase in viscosity in the event of prolonged storage, ultimately becoming jelly-like substances which are no longer able to flow.

It is known from an extensive article by S. Takano and K. Tsuji in J. Am. Oil. Chem. Soc. 60, 1807 (1983) that the highly viscous products have a high content of open-chain monocarboxylated compounds corresponding to formula (IIa):

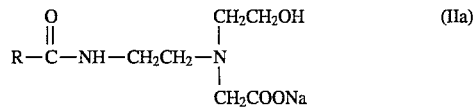

By contrast, low-viscosity products mainly contain a dicarboxylated product corresponding to formula (IIb):

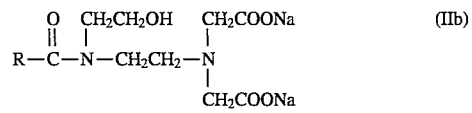

Accordingly, the problem addressed by the present invention was to provide an improved process for the production of low-viscosity, storable amphoteric surfactants. More particularly, the invention sought to provide amphoteric surfactants with a high content of compounds corresponding to formula (IIb).

DESCRIPTION OF THE INVENTION

The present invention relates to a process for the production of low-viscosity, storable amphoteric surfactants in which a) 1-hydroxyethyl-2-alkyl-2-imidazolines corresponding to formula (I):

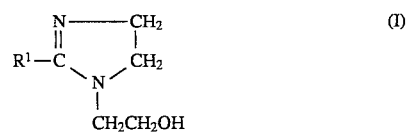

in which $R^1$ is an alkyl radical containing 5 to 21 carbon atoms, are quaternized or carboxymethylated with halogenated carboxylic acid salts and, at the same time, hydrolyzed with aqueous bases at a pH value in the range from 7.5 to 9 and b) the end reaction products are adjusted to a pH value of 5 to 7.

It has surprisingly been found that the careful control of the pH value both during the production of the imidazolinium betaines and during their storage results in the formation of products which are of low viscosity, even in highly concentrated form, and which show a constant low viscosity, even after storage for several weeks.

Starting Materials

1-Hydroxyethyl-2-alkyl-2-imidazolines are known substances which are obtained, for example, by condensation of fatty acids with aminoethyl ethanolamine. Typical examples of imidazolines which may be used as starting materials in the process according to the invention are the condensation products of aminoethyl ethanolamine with caproic acid, caprylic acid, capric acid, lauric acid, myristic acid, palmitic acid, stearic acid, isostearic acid, arachic acid and behenic acid and the technical mixtures thereof obtained, for example, in the pressure hydrolysis of native fats and oils. Imidazolines corresponding to formula (I), in which $R^1$ is a $C_{11-17}$ alkyl radical, based on technical cocofatty or tallow fatty acids are preferably used.

Halogenated carboxylic acid salts in the context of the invention are the sodium and/or potassium salts of haloacetic acid, halopropionic acid and/or halobutyric acid. Sodium chloroacetate is preferably used.

Quaternization, Carboxymethylation and Hydrolysis

The imidazolines and the halogenated carboxylic acid salts may normally be used in molar ratios of 1:1.5 to 1:3 and preferably 1:1.8 to 1:2.5. It has proved to be optimal to carry out the quaternization or carboxymethylation and the hydrolysis simultaneously at temperatures in the range from 70° to 85° C. and preferably at temperatures in the range from 78° to 83° C. Suitable aqueous bases are sodium hydroxide and/or potassium hydroxide, 5 to 55% by weight solutions and, more particularly, 30 to 50% by weight solutions of sodium hydroxide preferably being used. The quantity of base is determined by the content of halogenated carboxylic acid salt. The base and the salt are preferably used in a molar ratio of 0.9:1 to 1:1.2 and preferably in a molar ratio of 1:1 to 1:1.1. The function of the base is to form an inorganic salt, for example sodium chloride, with the halogen component of the carboxylic acid salt. If, nevertheless, it should be of advantage in practice to exceed the equimolar ratio, this may be done when a relatively high concentration of base is necessary to maintain the pH range regarded as critical. In addition, it has proved to be of advantage to add small quantities of citric acid, for example, to the solutions in order to buffer the mixtures.

In order to illustrate the findings on which the present invention is based, the process is described by way of example at this juncture:

A solution of aqueous sodium chloroacetate and citric acid is initially introduced. Beginning at 40° C., the imidazoline is added over a period of 30 minutes, the temperature rising to around 50° C. and the pH measured in the mixture to a value of 11.65. The temperature is then rapidly increased to 70° C., the pH value falling. The pH value is then kept constant at 8.5—as required by the process according to the invention—by addition of aqueous sodium hydroxide. The HPLC analysis of a sample taken at this time shows that monocarboxylate and predominantly dicarboxylate are present alongside one another. After a reaction time of about 7 h and a consumption of 90% by weight of total quantity of sodium hydroxide required to form the inorganic salt, the chromatogram shows only small amounts of unreacted imidazoline. The remaining quantity of base is added in one portion. Analysis of the reaction product, which is adjusted to pH 8.5 by addition of acid, shows a ratio of dicarboxylate to monocarboxylate of greater than 6. The viscosity is below 100 mPa·s. For storage, the pH value is lowered to 6.

If the reaction is carried out at pH values above 9, it is possible by HPLC to show that most of the imidazoline is hydrolyzed before quaternization can take place. The parallel carboxymethylation gives a highly viscous product which mainly contains compounds corresponding to formula (IIa).

If the reaction is carried out at pH values below 7.5, the establishment of an equilibrium between "betainized" and free imidazoline is observed. When sodium hydroxide is added, both species are rapidly hydrolyzed, resulting again in a high percentage of the compound corresponding to formula (IIa) (ratio of dicarboxylate to monocarboxylate <3).

If, by contrast, the reaction is carried out under the conditions of the process according to the invention (pH range 7.5 to 9), an equilibrium between betainized and free imidazoline is again established, although almost exclusively the betainized imidazoline is ring-opened under the reaction conditions. In accordance with the equilibrium position, betaine is reformed from the free imidazoline and, in turn, can be rehydrolyzed. In overall terms, therefore, the low-viscosity compound corresponding to formula (IIb) is predominantly formed.

Stability in Storage

The amphoteric surfactant concentrates of the prior art obtained on the basis of imidazoline almost all show a steady increase in viscosity in storage of which the rate is determined by the storage conditions, but especially by the ratio between the monocarboxylates and dicarboxylates (IIa) and (IIb). In the case of products corresponding to the prior art, the ratio of dicarboxylate to monocarboxylate typically falls from 3.2 to 1.4 after storage for 4 weeks at 60° C. This results in an increase in viscosity to more than four times the starting value. According to the invention, the sensitivity of (IIb) to hydrolysis can be counteracted by adjusting the product to a pH of 5 to 7 for storage. HPLC investigations have shown that the ratio of dicarboxylate to monocarboxylate and the content of free fatty acid remain constant under these conditions, even in the event of prolonged storage.

Industrial Applications

The amphoteric surfactants obtainable by the process according to the invention have low viscosities and remain stable in storage, even over prolonged periods. They are suitable for the production of surface-active formulations, more particularly dishwashing detergents and cleaning products and also hair-care and personal-hygiene products, in which they may be present in quantities of 0.1 to 25% by weight and preferably in quantities of 0.5 to 10% by weight, based on the particular product.

The following Examples are intended to illustrate the invention without limiting it in any way.

EXAMPLES

Example 1

In a 400 ml four-necked stirred reactor equipped with a reflux condenser, thermometer, pH electrode and dropping funnel, 77.7 g (666 mmoles) of sodium chloroacetate were dissolved in 170.2 g of water. After the addition of 0.6 g of citric acid monohydrate, 100 g (371 mmoles) of 1-hydroxyethyl-2-undecyl-2-imidazoline were uniformly added over a period of 25 minutes at 40° C., the temperature rising to 50° C. and the pH value (measured in the reaction mixture) to 11.7. The reaction mixture was then rapidly heated to 70° C., a reduction in the pH value being observed. The pH value was kept constant at 8.5 by addition of 38.9 g (486 mmoles) of sodium hydroxide in the form of a 50% by weight aqueous solution and the mixture was stirred for 240 minutes. The pH value was then increased to 9.0 and was kept constant for another 180 minutes by addition of sodium hydroxide. The total consumption of NaOH up to this time was 47.5 g (593.7 mmoles). After another 120 minutes (the pH value had meanwhile fallen to 8.3), another 5 g (62.5 mmoles) of sodium hydroxide were added and the mixture was stirred for 60 minutes. On completion of the reaction, the resulting clear liquid was adjusted to a pH value of 8.5 by addition of concentrated hydrochloric acid and water.

Characteristic Data of the Product
Viscosity: 120 mPa·s
Di/monocarboxylate ratio: 8.6
Water content (Fischer): 50.0 % by weight

Example 2

73.9 g (633 mmoles) of sodium chloroacetate dissolved in 152.8 g of water, 0.58 g of monohydrated citric acid and 100 g (352 mmoles) of an imidazoline, which had been obtained from a hydrogenated $C_{12/18}$ cocofatty acid and aminoethyl ethanolamine in accordance with DE-A 36 41 871, were reacted as in Example 1. To control the pH value, a total of 152.8 g (633.8 moles) of sodium hydroxide in the form of a 50% by weight aqueous solution was consumed. The end product (a clear liquid) was adjusted to a pH value of 6.5 with concentrated hydrochloric acid.

Characteristic Data of the Product
Viscosity: 40 mPa·s
Di/monocarboxylate ratio: 8.9
Water content (Fischer): 49.8 % by weight

Example 3

1,500 g of a product obtained as described in Example 1 were divided into 6 portions and adjusted to pH values in the range from 3 to 12 with hydrochloric acid and sodium hydroxide.

Equal portions of these products were stored for 2 weeks at temperatures of 5° to 60° C. The di/monocarboxylate ratio, the fatty acid content and the viscosity were then analyzed. The results are set out in Table 1.

Comparison Example C1

237.8 g (2.04 moles) of sodium chloroacetate dissolved in 450 g of water were reacted with 268 g (1 mole) of 1-hydroxyethyl-2-undecyl-2-imidazoline after addition of 8.4 g of citric acid, as described in Examples 1 and 9 of DE-B 40 38 983. After the imidazoline had been added, the mixture was stirred for 30 minutes at 80° C. 155.7 g (1.95 moles) of sodium hydroxide in the form of a 50% by weight aqueous solution were then uniformly added over a period of 120 minutes. After another 180 mins. reaction time, a pH value of 8.25 was established by addition of 50% by weight citric acid and the product was cooled A solids content of 50 0% by weight was established by addition of water.

The results of tests to determine stability in storage are set out in Table 2.

TABLE 1

Storage behavior of Example 3 according to the invention

| pH value | T °C. | DMR | Fatty acid % by weight | Viscos. mPa · s |
|---|---|---|---|---|
| 3.05 | 5 | 7.2 | 0.24 | 5100 |
| | 25 | 6.7 | 0.35 | 4500 |
| | 60 | 4.5 | 2.70 | 16300 |
| 5.07 | 5 | 8.3 | 0.29 | 280 |
| | 25 | 8.2 | 0.24 | 270 |
| | 60 | 6.6 | 0.40 | 1210 |
| 7.04 | 5 | 8.3 | 0.22 | 280 |
| | 25 | 8.2 | 0.25 | 250 |
| | 60 | 5.3 | 0.35 | 2150 |
| 8.59 | 5 | 8.2 | 0.24 | 155 |
| | 25 | 8.1 | 0.27 | 120 |
| | 60 | 3.3 | 1.00 | 12500 |
| 10.46 | 5 | 8.4 | 0.32 | 130 |
| | 25 | 8.4 | 0.34 | 120 |
| | 60 | 4.2 | 2.50 | 21000 |
| 12.0 | 5 | 4.1 | 2.60 | 35000 |
| | 25 | 3.8 | 3.50 | n.m. |
| | 60 | 0.7 | 8.4 | n.m. |

Legend:
T = Temperature
DMR = Di/monocarboxylate ratio
Viscos. = Viscosity cone/plate system at 25° C., Carri-Med viscosimeter
n.m. = Not measurable

TABLE 2

Storage behavior of Comparison Example

| pH value | T °C. | St. w | DMR | Fatty acid % by weight | Viscos. mPa · s |
|---|---|---|---|---|---|
| 8.25 | — | — | 3.2 | 1.1 | 380 |
| 8.10 | 60 | 1 | 2.6 | 2.1 | 16000 |
| 7.90 | 60 | 4 | 1.4 | 4.3 | 40000 |

Legend:
St. = Storage time
w = Weeks

What is claimed is:

1. A process for the production of a low-viscosity, storable amphoteric surfactant comprising the steps of: (1) simultaneously reacting a 1-hydroxyethyl-2-alkyl-2-imidazoline of the formula (I):

$$R^1 \underset{\underset{CH_2CH_2OH}{|}}{\overset{N}{\underset{N}{\bigtriangleup}}}$$ (I)

wherein $R^1$ is an alkyl radical having from about 5 to about 21 carbon atoms with a halogenated carboxylic acid salt in the presence of an aqueous base and maintaining the pH of the reaction mixture at a value of from about 7.5 to about 9 until completion of the reaction and then, (2) adjusting the pH of the reaction mixture to a value of from about 5 to about 7.

2. The process of claim 1 wherein $R^1$ is an alkyl radical having from 11 to 17 carbon atoms.

3. The process of claim 1 wherein said halogenated carboxylic acid salt is sodium chloroacetate.

4. The process of claim 1 wherein the molar ratio of said imidazoline to said halogenated carboxylic acid salt is from about 1:1.5 to about 1:3.

5. The process of claim 1 wherein step (1) is carried out at a temperature of from about 70° to about 85° C.

6. The process of claim 1 wherein in step (1), the pH is maintained by the addition of a 5 to 55% by weight aqueous sodium hydroxide solution.

7. The process of claim 1 wherein the molar ratio of said base to said halogenated carboxylic acid salt is from about 0.9:1 to about 1:1.2.

8. The process of claim 4 wherein said molar ratio is from about 1:1.8 to about 1:2.5.

9. The process of claim 5 wherein said temperature is in the range of from about 78° to about 83° C.

10. The process of claim 6 wherein the addition is carried out with a 30 to 50% by weight aqueous sodium hydroxide solution.

11. The process of claim 7 wherein said molar ratio is from about 1:1 to about 1:1.1.

12. The process of claim 1 wherein the aqueous base in step (1) is an aqueous sodium hydroxide solution; the molar ratio of said imidazoline to said halogenated carboxylic acid salt is from about 1:1.5 to about 1:3; the molar ratio of said base to said halogenated carboxylic acid salt is from about 0.9:1 to about 1:1.2; $R^1$ is an alkyl radical having from 11 to 17 carbon atoms; and step (1) is carried out at a temperature in the range of from about 70° to about 85° C.

13. The process of claim 12 wherein said halogenated carboxylic acid salt is sodium chloroacetate.

14. The process of claim 12 wherein the molar ratio of said imidazoline to said halogenated carboxylic acid salt is from about 1:1.8 to about 1:2.5; the molar ratio of said base to said halogenated carboxylic acid salt is from about 1:1 to about 1:1.1; and step (1) is carried out at a temperature in the range of from about 78° to about 83° C.

* * * * *